(12) United States Patent
Germond et al.

(10) Patent No.: US 7,498,162 B2
(45) Date of Patent: Mar. 3, 2009

(54) LACTIC ACID BACTERIA CAPABLE OF REDUCING AN INDIVIDUAL'S TENDENCY TO DEVELOP ALLERGIC REACTIONS

(75) Inventors: Jacques Edouard Germond, Crissier (CH); Blaise Corthesy, Lausanne (CH); Beat Mollet, Lausanne (CH); Rodolphe Fritsche, La Tour-de-Peilz (CH)

(73) Assignee: Nestec S.A., Vevey (CH)

( * ) Notice: Subject to any disclaimer, the term of this patent is extended or adjusted under 35 U.S.C. 154(b) by 392 days.

(21) Appl. No.: 10/362,249

(22) PCT Filed: Sep. 21, 2001

(86) PCT No.: PCT/EP01/10956

§ 371 (c)(1),
(2), (4) Date: Sep. 8, 2003

(87) PCT Pub. No.: WO02/24883

PCT Pub. Date: Mar. 28, 2002

(65) Prior Publication Data

US 2004/0071714 A1    Apr. 15, 2004

(30) Foreign Application Priority Data

Sep. 25, 2000    (EP) ................... 00120867

(51) Int. Cl.
*C12N 1/20*    (2006.01)
*A01N 63/00*    (2006.01)
(52) U.S. Cl. .................. 435/252.3; 424/93.1
(58) Field of Classification Search .............. 435/252.3; 424/93.1
See application file for complete search history.

(56) References Cited

U.S. PATENT DOCUMENTS 6,100,055 A * 8/2000 Guss et al. ................. 435/69.1
6,100,388 A * 8/2000 Casas et al. ................ 536/23.5

FOREIGN PATENT DOCUMENTS

| WO | WO 95/21926 | 8/1995 |
|---|---|---|
| WO | WO 96/32486 | 10/1996 |
| WO | WO 97/00078 | 1/1997 |
| WO | WO 97/09437 | 3/1997 |
| WO | WO 00/42863 | 7/2000 |

OTHER PUBLICATIONS

Plotkin et al (Vaccines, 1988, p. 571).*
Pouwels et al. article entitled: "Lactic acid bacteria as antigen delivery vehicles for oral immunization purposes" *International Journal of Food Microbiology*, 41 (1998) 155-167.
Maassen et al. article entitled: "Instruments for oral disease-intervention strategies: recombinant *Lactobacillus casei* expressing tetanus toxin fragment C for vaccination of myelin proteins for oral tolerance induction in multiple sclerosis" *Vaccine* 17 (1999) 2117-2128.
Gilbert et al. article entitled: "A New Cell Surface Proteinase: Sequencing and Analysis of the *prtB* Gene from *Lactobacillus delbrueckii* subsp. *bulgaricus*" *Journal of Bacteriology* Jun. 1996, p. 3059-3065.
Borel et al. article entitled: "Induction of Systemic Tolerance by Tolerogens" *Intestinal Immunology and Food Allergy*, Nestle Nutrition Workshop Series, vol. 34, pp. 179-189.

* cited by examiner

*Primary Examiner*—Mark Navarro
(74) *Attorney, Agent, or Firm*—Bell, Boyd & Lloyd LLP

(57) ABSTRACT

The present invention pertains to novel strains of lactic acid bacteria that are capable to reduce an individual's tendency to mount allergic reactions. In particular, the present invention relates to the generation of lactic acid bacteria strains that express proteins including tolerogenic peptides and the use thereof in reducing an individual's tendency to mount allergic reactions. The invention also pertains to food or pharmaceutical compositions containing said micro-organisms or active fractions thereof.

20 Claims, 3 Drawing Sheets

Peptide T1   H₂N-A-L-K-COOH
(139-141)

Peptide T2   H₂N-H-I-R-COOH
(146-148)

Peptide T3   H₂N-F-D-K-COOH
(136-138)

Peptide T4 (SEQ ID 1)   H₂N-I-I-A-E-K-COOH
(71-75)

Peptide T5 (SEQ ID 2)   H₂N-E-N-G-E-C-A-Q-K-COOH
(62-69)

Peptide T6 (SEQ ID 3)   H₂N-I-D-A-L-N-E-N-K-COOH
(84-91)

Peptide T7 (SEQ ID 4)   H₂N-G-L-D-I-Q-K-COOH
(9-14)

Peptide T8 (SEQ ID 5)   H₂N-A-L-P-M-COOH
(142-145)

Peptide T9 (SEQ ID 6), T10 (SEQ ID 7), T11 (SEQ ID 8)   H₂N-W-E-N-G-E-C-A,-Q,-K,-COOH
(61-67,-68,-69)

Peptide T12 (SEQ ID 9)   H₂N-T-P-E-V-D-D-E-A-L-E-K-COOH
(125-135)

Peptide T13 (SEQ ID 10)   H₂N-L-I-V-T-Q-T-M-K-COOH
(1-8)

Peptide T14 (SEQ ID 11)   H₂N-A-L-P-M-H-I-R-COOH
(142-148) = T8 (142-145) + T2 (146-148)

Peptide T15 (SEQ ID 12)   H₂N-I-P-A-V-F-K-COOH
(78-82)

Peptide T16 (SEQ ID 13)   H₂N-V-A-G-T-W-Y-COOH
(15-20)

Peptide T17 (SEQ ID 15), (SEQ ID 14)   H₂N-V-L-V-L-D-T-D-Y-K,-K-COOH
(92-99, 100)

Peptide T18 (SEQ ID 16)   H₂N-T-P-E-V-D-D-E-A-L-E-K-F-D-K-COOH
(125-138) = T12 (125-135) + T3 (136-138)

Peptide T19 (SEQ ID 17)   H₂N-A-A-S-D-I-S-L-L-D-A-Q-S-A-P-L-R-COOH
(25-40)

Fig. 1A

Peptide T20, T21  H₂N-W,-E-N-G-E-C-A-Q-K-COOH
(61, 62-69):S-S:(149-162)                          |
                 (SEQ ID 18)    H₂N-L-S-F-N-P-T-Q-L-E-E-Q-C-H-I-COOH Peptide T22 (SEQ ID 19)  H₂N-S-L-A-M-A-A-S-D-I-S-L-L-D-A-Q-S-A-P-L-R-COOH
(21-40)

Peptide T23 (SEQ ID 20)  H₂N-V-Y-V-E-E-L-K-P-T-P-E-G-D-L-E-I-L-L-Q-K-COOH
(41-60)

Peptide T24 (SEQ ID 21)  H₂N-L-S-F-N-P-T-Q-L-E-E-Q-C-H-I-COOH
(149-162)

Fig. 1B

LACTIC ACID BACTERIA CAPABLE OF REDUCING AN INDIVIDUAL'S TENDENCY TO DEVELOP ALLERGIC REACTIONS

BACKGROUND OF THE INVENTION

The present invention pertains to novel stains of lactic acid bacteria that are capable to reduce an individual's tendency to develop allergic reactions. In particular, the present invention relates to novel strains of lactic acid bacteria that express polypeptides including tolerogenic peptides and the use thereof in reducing an individual's tendency to develop allergic reactions. The invention also pertains to food or pharmaceutical compositions containing said micro-organisms or active fractions thereof.

Allergies are inappropriate reactions of the immune system to a variety of substances (allergens). Generally, individuals do not generate a substantial immune reaction against substances regularly encountered in the environment, such as pollen or food material, which non-reactivity is deemed to be mainly due to a suppressing mechanism of the immune system itself. However, in an impaired condition the immune system does not fulfil said suppressing activity (designated tolerance) resulting in a specific immune reaction against the allergen—the allergic reaction. Allergic reactions involve the release of biologically active compounds, such as the inflammation mediators histamine, leukotrienes and enzymes, from particular cells, mainly mast cells and basophil granulocytes, into surrounding tissue and vascular structures. Mast cells are dispersed throughout the individuals tissue whilst basophils circulate within the vascular system. Upon a sequence of events involving IgE antibodies the compounds/mediators are released from target mast cells ending up in pharmacological reactions.

In the past, the number of individuals suffering from allergy has increased, which is often attributed to an ever increasing atmospheric pollution caused by e.g. exhaust gases. Also, an extended consumption of proteinaceous material is deemed to contribute to said development, in particular to the growing occurrence of food allergy. In addition, the deficit in microbial infections encountered in developed countries has been suggested as another possible cause for the increase of atopic diseases.

Food allergies and even food intolerance of some kind have become quite common. The majority of the affected individuals have been found to exhibit an intolerance to certain constituents of foods with about 5 percent of the population even developing reactions to ingested substances which are sufficiently serious to require medical attention.

In recent years evidence has mounted that the major cause for food intolerance resides in the absorption of substances by the body that are normally excluded, which are, however, absorbed by the gastrointestinal tract in susceptible individuals. This mal-absorption is deemed to derive from defects in the tissue which lines the digestive tract (Peters et al., (1988) Can. J. of Gastroenterol. 2, 127; Olaison et al., (1990) Scand. J. of Gastroenterol. 25, 321; Hollander et al., (1986) Ann. of Int. Med. 105, 883). The recently identified capacity of epithelial cells lining the GI tract to process and present antigens might also account for the triggering of improper immune reactions leading to an inflammation and allergic outcome (Campbell et al., (1999) Immunol. Rev. 172, 315).

The manifestation of food allergy may involve substantially any tissue in the body. Because of its large absorptive area the gastrointestinal tract is likely to be the major site of absorption for offending substances. Many of the symptoms of food allergies are manifest in the digestive tract itself, but might also affect other tissues, including the skin and airways.

In the art different approaches are proposed to treat allergy, in particular food allergy.

One such approach aims at modifying the source of the allergenic material itself such that its allergic potential is reduced. This may be achieved by limiting or banning the food or components thereof, respectively, which would be the cause of such problems. A problem involved often resides in that the specific antigenic substance (allergen) in the respective food material is frequently not known so that in most cases it is not clear which component should be selectively removed.

In U.S. Pat. No. 5,480,660 is reported that the onset of the allergy in patients with allergies to wheat may be alleviated by eliminating or reducing, from flour, proteins having molecular weights of not more than 30,000 Da and proteins having a molecular weight of between 50,000 to 70,000 Da In JP 11 04 67 21 there is disclosed a method for reducing the allergeneicity of a protein containing food material, wherein the food material is mixed with wheat flour and the mixture is baked for more than 3 minutes at 180° C.

In U.S. Pat. No. 4,293,571 the preparation of a hypoallergenic composition is described, wherein a proteinaceous material is subjected to a hydrolysis treatment, the remaining, non hydrolysed proteins are subjected to coagulation by heat treatment followed by an ultrafiltration step to eliminate the coagulated material and macropeptides that might constitute allergens.

In U.S. Pat. No. 5,039,532 another process for the preparation of hypoallergenic food material is disclosed, wherein a whey product is subjected to enzymatic hydrolysis.

Yet, all these methods of treating the food material or even excluding it from the daily diet eventually prove to be difficult in practice, since they require diet revision, usually involving strict restrictive measures and may eventually affect the quality of life and/or inhibit the expected growth of the individual.

A different approach of treating food allergy and food intolerance is directed to restoring and maintaining the intestine's integrity such that food allergens essentially may not pass. In this respect U.S. Pat. No. 5,192,750 describes the use of N-acetyl glucosamine to enable the mucosa to form the necessary barrier to transmission of food allergens and to maintain normal function.

According to yet another approach of treating allergy vaccination of individuals against IgE molecules is suggested which inhibits the triggering of mast cells and basophils. To this end, WO 97/31948 proposes specific peptides for vaccination that resemble in their three dimensional conformation parts of the IgE molecule, immunoglobulins involved in the release of the mediators involved in the regulation of allergic and inflammatory reactions. It is conceived that the individual's own immune system will eventually form antibodies directed to said IgE molecules such that said IgE immunoglobulins are scavenged. However, said method harbors the disadvantage the antibodies formed may exhibit cross-reactivity with other immunoglobulin classes, such that the natural defence mechanisms of the individual may be adversely influenced.

In EP 99200130.5, a patent application owned by the present applicant, which has not yet been published, still another approach is disclosed. A hypoallergenic composition is proposed that contains a non-allergenic, extensively hydrolysed protein material and/or a free amino acid basis and at least one tolerogenic peptide of the respective allergenic protein. Although this composition provides many advantages over the prior art it is still difficult to obtain the tolerogenic peptide, which has to be produced for each batch de novo.

SUMMARY OF THE INVENTION

Therefore, there is a need in the art to provide improved means for treating allergy.

An object of the present invention therefore resides in providing such a means.

The above object has been solved by providing novel lactic acid bacteria strains that are capable to reduce an individual's tendency to develop allergic reactions. The novel lactic acid bacteria express a polypeptide that harbours a tolerogenic peptide such that the specific sequence and possibly configuration of the tolerogenic peptide is retained, the stability preserved and may thus be processed and recognized by the individual's immune system.

Additional features and advantages of the present invention are described in, and will be apparent from, the detailed description of the presently preferred embodiments and the drawings.

BRIEF DESCRIPTION OF THE FIGURES

FIGS. 1A and B shows the primary sequences of peptides contained in the respective fractions of the β-lactoglobulin hydrolyzate (vertical bars represent disulfide bonds).

DETAILED DESCRIPTION OF THE INVENTION

Figure 2:
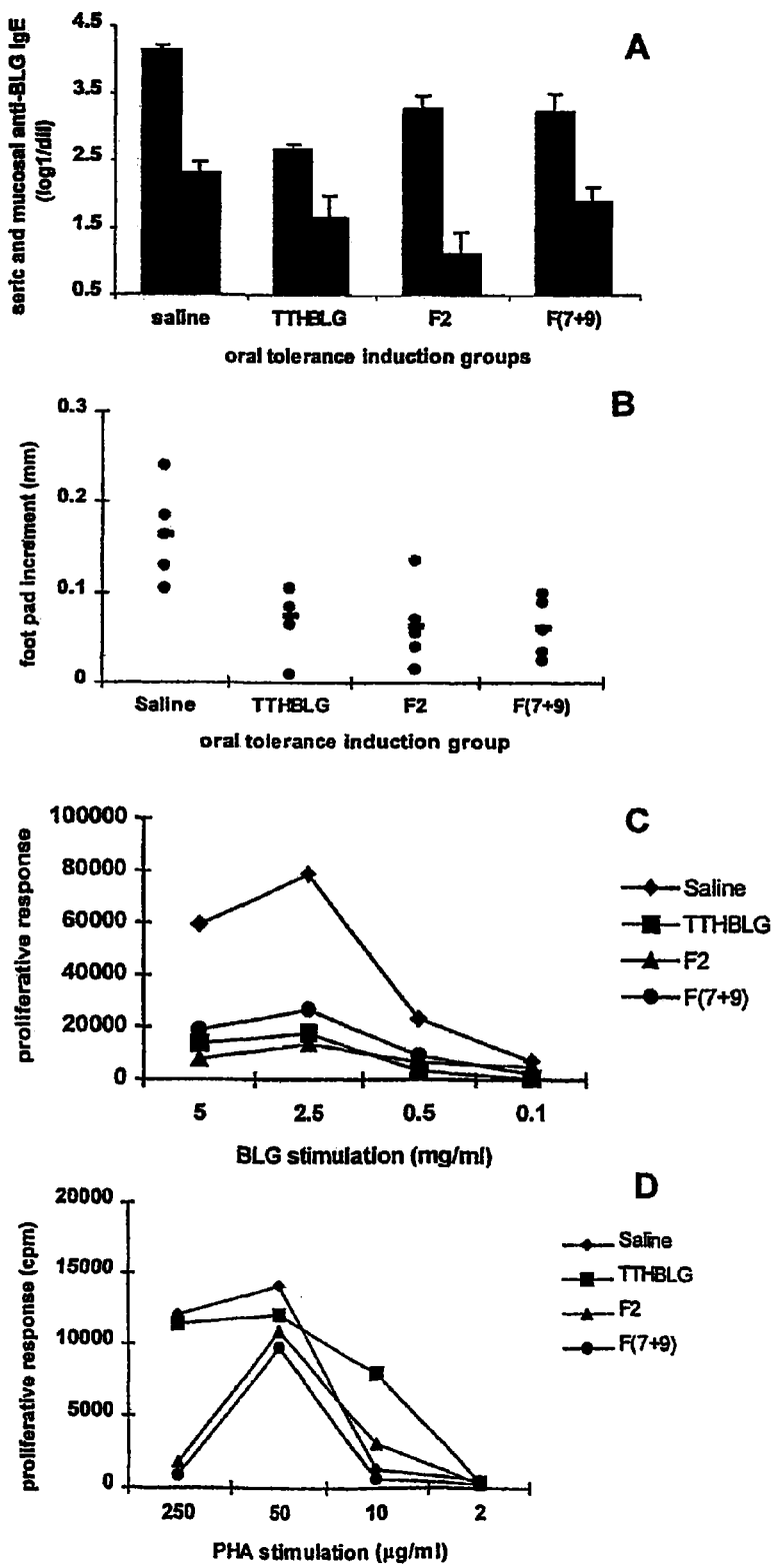
FIG. 2 shows the results obtained with tolerogenic peptides/peptide fractions in various experiments.

Lactic acid bacteria, in particular Lactobacilli and Bifidobacteria have been shown to modulate the immune system without leaving their lumenal habitat by producing messengers (cytokines) involved in the regulation of the immune system. Lactic acid bacteria do not trigger the production of pro-inflammatory cytokines, such as IL-8, TNF-α, MCP-1 and GM-CSF, but rather promote the production of inflammation inhibitory cytokines, such as TGF-β (Blum et al., (1999) Antonie van Leeuwenhoek 76, 199), with important implications regarding the maintenance of both the intestinal immune homeostasis and the epithelial barrier integrity (Planchon et al., (1999) J. Cell Physiol. 181, 55). Consistently, oral administration of lactobacilli homogenates was shown to exert a suppressive effect on mitogen-induced proliferation of mononuclear cells (Pessi et al., (1999) Appl. Environ. Microbiol. 65, 4725).

Lactic acid bacteria (LAB) may be used for heterologous (over-)production of proteins and peptides with systems to permit expression of a foreign gene based on chromosomal integration or episomal plasmid elements (see e.g. Kuipers et al., (1997) Tibtech 15, 140). Further, Lactic acid bacteria have a potential to colonize mucosal surfaces, and exhibit an intrinsic adjuvanticity associated with muramyl peptides resulting from peptidoglycan degradation.

Further, it has been shown that certain *Lactobacillus* strains promote antigen-specific immune responses, particularly in the IgA class (Majamaa et al., (1995) J. Pediatr. Gastroenterol. Nutr. 20, 333). The inability of human IgA complexed to antigens to activate complement may be of importance in the maintenance of the integrity of mucosal surfaces. This would prevent local inflammatory reactions including influx of leukocytes and release of immunological effectors that enhance mucosal membrane permeability due to tissue damage. In addition, through this immune exclusion mechanism, IgA might limit further absorption of bystander antigens and thus abrogate anaphylactic reactions mediated by antibodies of IgE and IgG isotypes.

Moreover, lactobacilli have been shown to potentiate the production of IFN-gamma by isolated T cells (Halpern et al., (1991) Int. J. Immunother. 7, 205). Recently, IFN-gamma has been shown to inhibit TNF-alpha release of intestinal mucosal mast cells (Bissonnette et al., (1995) Int. Arch. Allergy Immunol. 107, 156). Increased IFN-gamma secretion might prevent detrimental effects of TNF-alpha (Hernandez-Pando et al., (1994) Immunology 82, 591), and consequently counteract the permeability disorder associated with food allergy. For instance, impairment of the intestine's barrier against antigen uptake in atopic eczema may be the key determinant in exaggerated immune responses to common dietary and environmental allergens.

During the extensive studies leading to the present invention the inventors have therefore devised means to combine the advantageous properties of lactic acid bacteria with the potential of tolerogenic peptides to generate a powerful agent to reduce or even minimize an individual's tendency towards allergic reactions.

The lactic acid bacterium to be used in the present invention preferably belongs to the *Lactobacillus* group or Bifidobacterium group or *Lactococcus* group, and is more preferably derived from the groups of *L. acidophilus, L. johusonli, L. gasseri; L. casei, L. paracasei* or *L. reuteri*, all of human or animal origin, respectively.

The tolerogenic peptide, which is a peptide derived from a given protein causing allergy in an individual generally has a size of about 200 to 6000 Da and is a peptide capable to induce tolerance at least to the protein, from which it is derived. In addition, tolerance will be induced to any material having the same antigenic determinant than that represented by the specific tolerogenic peptide as well. According to the present invention this peptide is inserted by recombinant means into a polypeptide synthesized in the lactic acid bacterium, which polypeptide may be endogeneous or exogeneous to the bacterium. The tolerogenic peptide is inserted in such a way that it is presented on the periphery of the resulting recombinant polypeptide such that it may be recognized by the immune system.

The polypeptide may be expressed in the lactic acid bacterium according to methods well known in the art. For example the commercially available vectors pNZ124 (Platteuw et al., (1994) Appl. Env. Microbiol. 60, 587), pGK12 (Walke et al., (1996) FEMS Microbiol. 138, 233,) or pG+host9 (Maguin et al., (1996) J. Bacteriol 178, 931) may be used for episomal expression. Yet, having in mind the superior stability of chromosome integration, this way of doing could be preferred for the recombinant gene coding for the respective polypeptide. For integration into the chromsomome homologous recombination may be applied by e.g. using an recombinant gene from Lactic acid bacteria, containing the tolerogenic peptide and replacing the endogeneous gene. Yet, methods for introducing recombinant genes into a host's chromosome are well within the skilled personas skill.

The polypeptide may be a protein normally expressed to reside within the cell but may well be a polypeptide that is secreted by the lactic acid bacterium or that is inserted into the cell wall thereof, with the part containing the tolerogenic peptide being located in the extracellular section. Examples of polypeptides to be used in the present invention are pepN, pepX, lactate dehydrogenase or β-galactosidase, or a member of the class of bacteriosins or S-layer protein or a cell wall anchored protease.

The nature of the polypeptide is not crucial with the proviso that the tolerogenic peptide may be inserted such that it is accessible for the immune system. However, once a suitable tolerogenic peptide has been identified it is well within the ordinary skill to arrange the tolerogenic peptide in such a location. To this end, the skill person will consult three dimensional models of the polypeptides, into which the tolerogenic peptide is to be inserted and based on such information will design a corresponding recombinant protein.

In a preferred embodiment the recombinant polypeptides are secreted or are arranged in the cell wall of the bacterium such that the tolerogenic peptide is constantly presented to the environment.

The tolerogenic peptide is derived from food material causing allergic reaction. Yet, it is not essential that its amino acid sequence corresponds to that found in the native protein, but any peptide sequence having essentially the same amino acid sequence and possibly three dimensional conformation as the starting peptide or a derived polypeptide therefrom which exhibits essential the same results, i.e. induces a reduction in the allergic response, will be suitable for the given purpose.

As preferred sources for tolerogenic peptides milk, soja, peanut, crustaceei, fish, meat, sesam or whey may be mentioned, such as e.g. β-lactoglobulin, bovine serum albumin or casein.

In order to identify tolerogenic peptides the allergenic material of interest is first subjected to an enzymatic hydrolysis to a degree of about 10 to 50% and the residual enzymatic activity in the protein mixture is inactivated by e.g. heat treatment. The protein hydrolysate solution is clarified and further purified if desired. The peptides thus obtained are separated by e.g. submitting the solution to a precipitation treatment or passing it through a chromatography column.

Subsequently, th fractions containing different peptides are tested for their tolerogenic properties by testing them in an animal model. To this end animals, such as mice are fed with the respective peptide fractions, and subsequently, are immunized with the allergen and the response thereto is measured, such as by a change in the outer appearance or by specifically measuring IgE levels in the animals. As a result, tolerogenic peptide fractions will reduce the animal's tendency to react against the allergen, so that the respective peptide (fraction) may be determined.

Once a tolerogenic peptide and its amino acid sequence has been verified the DNA-sequence of the polypeptide to be expressed in the lactic acid bacterium is inserted by genetic engineering into the gene coding for the bacteria protein carrier. Methods and techniques for manipulating DNA sequences and expressing proteins in micro-organis are described in Sambrook et al., A Laboratory Manual Cold Spring Harbor (1992).

The present invention also relates to a food and pharmaceutical composition containing at least one of such a recombinant lactic acid bacterium.

The bacterial strain may be included in the composition in an amount ranging from $10^5$ to $10^{12}$ cfu (colony forming unit) per g of the material. Likewise a supernatant of a culture of the lactic acid bacterium or an active fraction thereof may be included in the composition.

The food composition may be milk, yoghurt, curd, cheese, fermented milks, milk based fermented products, ice cream, fermented cereal based products, milk based powders, infant formulae or, in case of animals, pet food.

The pharmaceutical composition may be in the form of tablets, liquid bacterial suspensions or preparations comprising parts of the bacteria, such as merely the cell wall fraction obtained by lysing the bacterial dells and collecting the cell wall component, dried oral supplements, wet oral supplements, dry tube feeding or wet tube-feeding.

The route of administration for the pharmaceutical preparation is oral, but may also be nasal.

The present invention also envisages vaccines, comprising the bacteria of the present invention or parts thereof. The bacteria may be in live form, or may be attenuated, i.e. weakened in their growth potential if desired. As parts of th bacteria, primarily the cell wall harboring the antigen of interest shall be applied. The cell wall may be easily obtained by lysing the cells and separating the different components thereof.

The following examples further illustrate the invention without limiting it thereto.

EXAMPLE 1

Isolation of Tolerogenic Peptides a) Isolation of Peptides 220 g β-lactoglobulin (Sigma) was dissolved in bidistilled water at a concentration of 5% (w/w). To the resulting solution TPCK treated trypsin was added using an enzyme/substrate (E/S) ratio of 1/100 (w/w) and the solution was incubated at 40° C., pH 7.6 under constant stiring. After 1 hour the same amount of enzyme was added to yield a final (E/S) ratio of 2/100. Incubation was continued for another 4 hours and the enzyme was inactivated by heat treatment (85° C., 5 min) to stop the reaction. The entire tryptic hydrolysate was subsequently lyophilized and the resulting peptidic products were separated by preparative chromatography on a cationic resin.

15 different peptidic fractions were obtained, ranging from about 2 to 23 amino acids (from about 240 to 2720 Da). The individual fractions were nanofiltered, diafiltered, dialyzed, again lyophilized and stored dry at room temperature until use. The factions were also characterized for their peptide content using reverse phase High Performance Liquid Chromatography (HPLC). In total 15 fractions (F1-F15) were collected containing as the major component the peptides (T) indicated.

| Fractions | F1 | F2 | F3 | F4 | F5 | F6 | F7 | F8 | F9 | F19 | F11 | F12 | F13 | F14 | F15 |
|---|---|---|---|---|---|---|---|---|---|---|---|---|---|---|---|
| Masses (g) | 52 | 13.9 | 11 | 11.8 | 2.57 | 1.94 | 4.37 | 13.1 | 5.01 | 6.53 | 1.05 | 3.46 | 1.9 | 2.67 | 28.8 |
| Enriched pepticle | — | T6 T17 T18 | T23 | T23 | — | T7 | T20 T9 | T9 T21 T24 | T12 T12 T24 | T10 T21 | T11 T21 | T10 | T10 T11 | T10 T11 | — |

The peptides were isolated and sequenced. The sequences thereof are indicated in FIG. 1 Various peptides proofed to be tolerogenic, in different experimentations, which are described in detail in Pecquet R, Bovetto L, Maynard F, Fritsché R., Peptides obtained by tryptic hydrolysis of bovine B-lactoglobulin induce specific oral tolerance in mice, J. Allergy Clin Immunol (2000) 105:514-21, which reference is incorporated herewith byway of reference.

b) Synthesis of Tolerogenic Peptides

Three tolerogenic peptides of β-lactoglobulin (BLG) T6, T17 and T6/T17 as identified in the above reference as well as a control peptide T13 were chemically synthetised with flanking residues from the BLG sequence, as well as an extra Cys residue, as listed below:

```
T6 (SEQ ID 22)
C F K I D A L N E N K V S R
      84              91

T17 (SEQ ID 23)
C N K V L V L D T D Y K K Y S
      92                100

T6/T17 (SEQ ID 24)
C F K I D A L N E N K V L V L D T D Y K K Y S
      84                                100

T13 (SEQ ID 25)
L I V T Q T M K S R C
1               8
``` c) Animal Testing

For assessing the tolerogenic properties of the various peptides female Balb/c mice were used, obtained from IFFA-Crédo (L'Abresle France). The animals were all bred and raised on a milk free diet. At the beginning of the experiments the animals were 3 weeks old. They received by gavage native β-lactoglobulin (5 mg/g of body weight), various amounts of digested β-lactoglobulin and various amounts of the different peptides obtained under a) above. Control mice were fed saline water. After 5 days on such a diet all mice were immunized with β-lactoglobulin and ovalbumin (grade V, Sigma) as a non related antigen in order to assess the specificity of the immune response. A delayed type hypersensitivity evaluation (DTH) was performed 21 days after the systemic challenge by comparing the thickness of the left rear footpad, prior to and after the immunization. 24 hours after the immunization the foot pad thickness of the animals were measured (expressed in Δ thickness (mm)). Subsequently, blood was taken from all mice, followed by talking the spleens, that were pooled according to group treatment. Splenocyte specific proliferation assays were performed for each group. The intestinal contents were individually collected. Serum and intestinal samples were individually frozen at −80° C. until performance of the respective assays. Anti-β-lactoglobulin IgE and anti-ovalbumin IgE levels were determined both in serum and intestinal samples.

d) IgE antibody Assays

The serum and intestinal fluids were diluted and assayed in duplicate for anti-β-lactoglobulin and anti-ovalbumin IgE antibodies using ELISA. Pooled samples of 20 non immunized mice were used as negative controls. The titers were determined by calculating the dilution of the sample, that gave twice the absorbance of the negative control. The titers were expressed as the log10 of the reciprocal of he dilution e) Cell Cultures Spleen cell solutions were homogenized in PBS and purified. The cells were co-cultured in the presence of β-lactoglobulin or phytohemagglutinin A. Tritiated thymidine ([$^3$H]-Thy (Amersham, Zürich) was added during the last 6 hours of culture and the plates were harvested and analyzed by scintillation counting. Stimulation indices were calculated as the ratio of blank-substracted test and control levels expressed as the mean cpm of [$^3$H]-Thy incorporated by triplicate cultures.

f) Tolerance Induced by Oral Administration of Synthetic Peptides

The synthetic peptides were analysed for their tolerogenic capacity in the parenteral mouse model. Following results were obtained:

|  | IgE titer (log) (test/control) | Spleen lymphocyte SI (test/control) | MLN lymphocytes SI (test/control) |
|---|---|---|---|
| T-6 | 3.24/3.39 | 0.53 | 029 |
| T-17 | 2.67/3.39 | 0.31 | 0.41 |
| T-6/T-17 | 3.40/3.39 | 0.92 | 0.81 |
| T-13 | 3.20/3.39 | 1.70 | 0.87 |

SI: Stimulation Index
MLN: Mesenteric Lymph Node

One can see that synthetic peptide T-17 reduced both IgE production and T cell proliferation whereas peptide T6 suppressed only the T cell response. In contrast, peptide T-13, the control peptide, did not induce oral tolerance to BLG.

EXAMPLE 2

Construction of Recombinant Polypeptide

The peptides T6 and T17 identified in example 1 as exhibiting tolerogenic properties, were fused with a cell surface anchored protease to be displayed at the surface of a bacteria. As a negative control peptide T13, constituting part of the N-terminus of β-lactoglobulin was used.

The cell surface anchored protease (above) was that of *Lactobacillus bulgaricus*, the sequence of which was published in Gilbert et al., (1996) J. Bacteriol, 178, 3059-3065. This protein was characterized as a 2000 amino acids protein, being composed of a leader peptide of 33 amino acids (pre-region) responsible for cell export of the enzyme, followed by a series of 154 amino acids (pro-region) which is responsible, upon cleavage, for the activation of the proteolytic activity of the enzyme and 700-800 amino acids for the active site. The subsequent region (around 1000 amino acids) has been suggested to play a role in the specificity of cleavage and transport in the cell of the generated peptides and to also span the cell wall. The protease is cell wall anchored by its carboxyl end and with the last 200 amino acids being responsible for the specific covalent binding to the cell wall peptidoglycan structure.

The protease gene was first amplified with its promoter by using the following two primers:

```
                                          (SEQ ID 26)
5'-TTTTGTGGATCCTTAACTTCATAGCACG-3'
(upstream the promoter of the gene, carrying a
BamHI site)
```

-continued

```
5'-ATATTATCTAGAATTGAATAGATGCC-3'                    (SEQ ID 26)
(downstream the rho-independent terminator of the
gene, carrying a XbaI site)
```

The amplification product was cleaved with BamHI and XbaI and cloned in the lactic acid bacteria vector pNZ124, that had been digested with the same restriction enzymes, and eventually introduced by electroporation into plasmid-free (beta-galactosidase and protease negative) *Lactococcus lactis*.

The region of the active site of the cloned protease was replaced by the sequence of the peptide/polypeptide of interest. To achieve this, the cloned protease was cleaved with NheI which is located 50 bp downstream the sequence of the cleavage site of the leader peptide and PvuI, 800 bp further downstream. A DNA sequence coding for the peptides of interest (up to 10 amino acids) was, inserted between the two restriction sites as two oligonucleotides, which were designed such as to generate the two restriction sites at their ends once they are hybridized. The design of the oligonucleotides takes into account that upon ligation to the protease gene the reading frame of the recombinant protein remains open.

Insertion of larger polypeptides was effected by DNA amplification using primers containing the two restriction sites. The amplification product was cleaved with the restriction enzymes. In both cases the DNA fragments were ligated to the protease gene and introduced by electroporation into *Lactococcus lactis* and *Lactobacillus johnsonii*.

Recombinant plasmid constructs comprising the peptides T6 and T17, respectively, have been deposited on Sep. 22, 2000 under the Budapest Treaty with the Institute Pasteur and received the deposit no. CNCM I-2563 and CNCM I-2564, respectively.

EXAMPLE 3

Transformation of *Lactococcus lactic* and *Lactobacillus johnsonii*

For transformation purposes *Lactococcus lactis* strain (MG1363, plasmid free) and *Lactobacillus johnsonii* strain La1 (available from the Institute Pasteur under the accession no CNCM I-1225) was grown over night in MRS broth at 37° C. in a GasPak anaerobic system. An aliquot of this culture was used to inoculate another culture broth (MRS) containing 0.5 M sucrose. After an additional re-inoculation at 2°/ into 200 ml MRS+0.5 M sucrose the culture was grown to an $OD_{595}$ of 0.6. The cells were collected by centrifuging at 5000 rpm at 4° C. for 10 min, the pellet was washed once with ½ volume of a solution containing 1 M sucrose and 2.5 mM $CaCl_2$, once with ¼ volume of a solution containing 1 M sucrose, 2.5 mM $CaCl_2$) and the pellet obtained after centrifugation was resuspended in 3.5 ml of a solution of 1 M sucrose, 2.5 mM $CaCl_2$+0.459 ml 87% glycrol (10% final concentration). The cells were either be directly used for transformation or frozen at −80° C.

For the electroporation 40 µl of cells were mixed with 10-100 ng of DNA (in <5 µl volume) and transferred into an ice-cold 0.2 cm electroporation cuvette. Pulses at 200 Ω, 25 µF, 2.5 kV in ice-cold 0.2 cm electroporation cuvette were applied. To the cuvette 1 ml of MRS+20 mM $MgCl_2$, 2 mM $CaCl_2$ was added and the suspension was incubated for 2-3 hours at the appropriate temperature (at 30° C. for *Lactococcus lactis* and 37° C. for *Lactobacillus johnsonii*. When ts plasmids (pG+host9) are used incubation is at 30° C.). 10 µl and 100 µl aliquots, respectively, were plated on MRS agar plates containing the appropriate antibiotic upon transformation of plasmidic DNA and 100 µl and 500 µl, respectively, upon transformation with ligation mix. The plates were incubated anaerobically for 24-48 h at the same temperature as above.

As a selection medium MRS with erythromycin (2.5 µg/ml) or MRS with kanamycin (5 µg/ml) was used.

EXAMPLE 4

Generation of Rat Antisera and Monoclonal Antibodies Against Tolerogenic BLG Peptides The BLG peptides T6, T17, T6/T17 and T13 (outlined in example 1) were coupled to maleimide-activated KLH and were used together with Titermax adjuvant to immunize rats fed on lactic protein-free diet. Blood samples, taken at 2 weeks intervals up to 115 days after the first immunisation were shown by ELISA to contain antibodies specific to BLG peptides.

Anti-T6 and anti-T13 antisera also reacted with both the native (ELISA) or denatured (SDS-PAGE+Western blot) form of BLG. Anti-T6 and anti-T17 were shown to specifically recognize BLG peptides expressed at the surface of the recombinant *L. lactis*. The result are shown in table I.

TABLE I

Reactivity f anti β-lactoglobulin peptides antisera

| Antiserum specific for | T6 | | | T17 | | | T6/17 | | | T13 | | |
|---|---|---|---|---|---|---|---|---|---|---|---|---|
| Rat number | A1 | A2 | A3 | B4 | B5 | B6 | C7 | C8 | C9 | D10 | D11 | D12 |
| T6 (ELISA) | +++ | +/− | + | − | NT | NT | − | NT | NT | − | NT | NT |
| T17 (ELISA) | − | NT | NT | + | − | − | +++ | NT | NT | − | NT | NT |
| T6/17 (ELISA) | +++ | NT | NT | + | NT | NT | +++ | + | − | − | NT | NT |
| T13 (ELISA) | − | NT | NT | − | NT | NT | − | NT | NT | + | + | +/− |
| Nat BLG (ELISA) | +++ | +/− | +++ | +/− | − | − | − | − | − | + | + | +/− |
| Den. BLG (SDS-PAGE + WB) | +++ | NT | ++ | − | NT | NT | − | NT | NT | +/− | +++ | ++ |
| Ll/T6 (ELISA) | +/− | − | +++ | − | NT | NT | − | − | − | − | NT | NT |

TABLE I-continued

Reactivity f anti β-lactoglobulin peptides antisera

| Antiserum specific for | T6 | | | T17 | | | T6/17 | | | T13 | | |
|---|---|---|---|---|---|---|---|---|---|---|---|---|
| Rat number | A1 | A2 | A3 | B4 | B5 | B6 | C7 | C8 | C9 | D10 | D11 | D12 |
| LI/T17 (ELISA) | – | NT | NT | + | – | – | – | – | – | – | NT | NT |
| LI/T13 (ELISA) | – | NT | NT | – | NT | NT | – | NT | NT | – | – | – |

ELISA/OD490 nm (15'/37° C.)
+++ >0.3
++ 0.2-0.3
+ 0.1-0.2
+/– 0.05-0.1
– <0.1
NT not tested
nat. BLG 3x cristallized BLG (Sigma) dissolved in PBS
den. BLG 3x cristallized BLG (Sigma) diluted and boiled in SDS sample buffer
LI/T Recombinant *Lactococcus lactis* bearing *Lactobacillus bulgaricus* proteinase with BLG peptide insert For producing hybridomas secreting anti-BLG peptide monoclonal antibodies spleens were recovered from the immunized rats. The spleen cells were fused with myeloma cells according to standard techniques and a first round of screening already allowed the identification of cell populations producing either anti-T6 or anti-T17 antibodies. Cloning of these cells was achieved using a cell sorter to guarantee the presence of 1 single cell per well.

EXAMPLE 5

Detection of Tolerogenic Peptides by Antibodies

In order to determine, whether the lactic acid bacteria express the tolerogenic peptides in a manner so as to be accessible by and recognized by antibodies, bacteria containing the recombinant gene were grown in a 50 ml culture and the cells were collected by centrifugation. The cells were subsequently washed two times with 50 ml TBS and the cells were eventually suspended in 6 ml TBS. 75 µl of the suspension was transferred into a well (half well flat-bottom ELISA plate) and the plates were left without lid for 24 hours at 37° C. so that the well fell dry. The plates were washed 3 times with TBS/PBS until unbound bacteria were washed out and the wells were subsequently subjected a blocking treatment with TBS-casein (1.5 g/l) for 2 hours at 37° C. To the w lls a rat antiserum containing antibodies directed to the specific peptides was added. The wells were incubated over night at RT, using a dilution in TBS-Casein containing 0.2% Tween 20. Subsequently, the wells were washed three times with TBS and developing antibodies (HRP-conjugated goat anti-rat IgG) were added to the wells followed by an incubation at 37° C. diluted in TBS-casein solution containing. 0.2% Tween 20. The wells were washed three times with TBS and developed with OPD/H$_2$O$_2$ and read at 490 nm.

It could be observed that both strains of *Lactococcus lactis* and *Lactobacillus johnsonii* showed a positive reaction indicating that the tolerogenic peptide is recognized by antibodies.

EXAMPLE 6

Preparation of a Rabbit Antiserum Directed to the Amino Acid Residues 472-659 of *L. bulgaricus* prtB Proteinase The prtB target sequence (bp 1414-1977) encoding amino acid residues 472-659 (amino acid number 1 is the initiation methionine) was amplified by PCR using pMD114 as a template and the upstream primer (prtB5'-1414) of sequence
5'-GCGGATCCGGCTTGGGCGGTGCAGATG-3'
(SEQ ID 28) (containing a 5'-BamHI site), and downstream primer (prtB3'-1977) of sequence
5'-CGCAAGCTTGTGCGAAGTGTTCATGGC-3'
(SEQ ID 29) (containing a 5'-HindIII site).

The specific PCR product was obtained using Taq DNA polymerase (Perkin-Elmer) using 3 cycles consisting in a denaturation step at 95° C. for 30 s, a primer annealing step at 56° C. for 30 sec. and an extension step at 72° C. for 45 sec, followed by 27 cycles with an annealing step brought to 60° C.

After desalting and removal of primers and dNTPs (High Pure PCR Product Purification Kit, Roche), the sample was digested with BamHI and HindIII, then subjected to agarose gel electrophoresis and the DNA bands of interest were recovered from the gel (E.Z.N.A. Gel Extraction Kit, Peqlab).

The purified amplification product was ligated between the BamHI and HindIII sites of the pQE-9 *E. coli* expression vector (Qiagen), downstream to a sequence encoding a 6-histidine tag.

*E. coli* strain M15 [pREP4] was transformed with this vector and expression of the heterologous protein obtained upon 1 mM IPTG-mediated induction of the culture.

The cells of a 1-liter culture were pelleted and lysed under denaturing conditions (8M urea). A cleared lysate was obtained by centrifugation and was loaded onto Ni$^{2+}$-NTA agarose beads (Qiagen), equilibrated at pH 8.0, allowing the binding of the 6-histidine-tagged protein. After a washing step at pH 6.3, the recombinant protein was eluted at pH 4.5.

The material was neutralized with 100 mM Tris-Cl (pH 7.5), quantified by bicinchoninic acid protein assay (Pierce) and its concentration adjusted to 1 mg/ml using the same buffer.

The antigen was emulsified in complete Freund's adjuvant and administered by multiple intradermic injection to two rabbits. Injections were performed at day 0, 14, 28 and 56. Final bleeding occurred at day 80.

Reactivity of the antiserum, which was surprisingly strong, was confirmed both by ELISA, on recombinant Lc expressing *L. bulgaricus* prtB proteinase at their cell surface, and by immunoblotting, on the culture supernatant of recombinant Lc expressing a secreted form of the proteinase.

What claimed is:

1. A bacterial strain of a lactic acid bacterium group, expressing a polypeptide, said polypeptide comprising a tolerogenic peptide heterologous to said polypeptide, such that the peptide is stabilized towards degradation by stomach/duodenal enzymes, and retains its tolerogenic properties and is displayed at the periphery of said polypeptide, wherein the peptide is T1.

2. The bacterial strain according to claim 1, which is selected from the group consisting of *Lactobacillus* and *Bifidobacterium*.

3. The bacterial strain according to claim 1 wherein the tolerogenic peptide is derived from a food material.

4. A food composition comprising a bacterial strain of a lactic acid bacterium group, expressing a polypeptide, said polypeptide comprising a tolerogenic peptide heterologous to said polypeptide, such that the peptide is stabilized towards degradation by stomach/duodenal enzymes, and retains its tolerogenic properties and is displayed at a periphery of said polypeptide, or a supernatant thereof, wherein the peptide is T1.

5. The food composition according to claim 4, which is selected from the group consisting of milk, yoghurt, curd, cheese, fermented milks, milk based fermented products, ice cream, fermented cereal based products, milk based powders, infant formulae and pet food.

6. The food material according to claim 4, wherein the bacterial strain is contained in an amount ranging from $10^7$ to $10^{11}$ cfu/dosage form.

7. A composition comprising a bacterial strain of a lactic acid bacterium group, expressing a polypeptide, said polypeptide comprising a tolerogenic peptide heterologous to said polypeptide, such that the peptide is stabilized towards degradation by stomach/duodenal enzymes, and retains its tolerogenic properties and is displayed at a periphery of said polypeptide, or a supernatant thereof, wherein the peptide is T1.

8. The composition according to claim 7, wherein the bacterial strain is contained in an amount ranging from $10^{10}$ to $10^{12}$ cfu/dosage form.

9. A method of making an ingestable carrier, the method comprising the step of adding to the ingestable carrier a lactic acid bacterium group, expressing a polypeptide, said polypeptide comprising a tolerogenic peptide heterologous to said polypeptide, such that the peptide is stabilized towards degradation by stomach/duodenal enzymes, and retains its tolerogenic properties and is displayed at a periphery of said polypeptide to produce the ingestable carrier, wherein the peptide is T1.

10. A method of making a food composition, the method comprising the step of providing a food composition and adding to the food composition a lactic acid bacterium group, expressing a polypeptide, said polypeptide comprising a tolerogenic peptide heterologous to polypeptide, such that the peptide is stabilized towards degradation by stomach/duodenal enzymes, and retains its tolerogenic properties and is displayed at the periphery of said polypeptide to produce an ingestable carrier, wherein the peptide is T1.

11. The method of claim 10, wherein the composition is administered either through an oral or a nasal route.

12. A composition comprising a bacterial strain of a lactic acid bacterium group, expressing a polypeptide, said polypeptide comprising a tolerogenic peptide heterologous to polypeptide, such that the peptide is stabilized towards degradation by stomach/duodenal enzymes, and retains its tolerogenic properties and is displayed at a periphery of said polypeptide, wherein the peptide is T1, and wherein a cell membrane fraction of lysed bacteria are utilized.

13. A method for the treatment of an allergy in an individual, the method comprising the steps of administering to the individual having the allergy a therapeutically-effective amount of a bacterial strain of a lactic acid bacterium group, expressing a polypeptide, said polypeptide comprising a tolerogenic peptide heterologous to said polypeptide, such that the peptide is stabilized towards degradation by stomach/duodenal enzymes, and retains its tolerogenic properties and is displayed at a periphery of said polypeptide, wherein the peptide is T1.

14. The method according to claim 13, wherein the bacterial strain is selected from the group consisting of *Lactobacillus* and *Bifidobacterium*.

15. The method according to claim 13, wherein the tolerogenic peptide is derived from a food material.

16. The method of claim 13, wherein a food composition containing the bacterial strain is administered either through an oral or a nasal route.

17. The method of claim 16, wherein the food composition is selected from the group consisting of milk, yoghurt, curd, cheese, fermented milks, milk based fermented products, ice cream, fermented cereal based products, milk based powders, infant formulae and pet food.

18. The food composition of claim 4, wherein the bacterial strain is contained in an amount ranging from $10^7$ to $10^{11}$ cfu/dosage form.

19. The method of claim 13, wherein the composition is administered via an oral route.

20. The method of claim 13, wherein the composition is administered via a nasal route.

* * * * *

SEQUENCE LISTING

<160> NUMBER OF SEQ ID NOS: 29

<210> SEQ ID NO 1
<211> LENGTH: 5
<212> TYPE: PRT
<213> ORGANISM: bovine

<400> SEQUENCE: 1

Ile Ile Ala Glu Lys
 1               5

<210> SEQ ID NO 2
<211> LENGTH: 8
<212> TYPE: PRT
<213> ORGANISM: bovine

<400> SEQUENCE: 2

Glu Asn Gly Glu Cys Ala Gln Lys
 1               5

<210> SEQ ID NO 3
<211> LENGTH: 8
<212> TYPE: PRT
<213> ORGANISM: bovine

<400> SEQUENCE: 3

Ile Asp Ala Leu Asn Glu Asn Lys
 1               5

<210> SEQ ID NO 4
<211> LENGTH: 6
<212> TYPE: PRT
<213> ORGANISM: bovine

<400> SEQUENCE: 4

Gly Leu Asp Ile Gln Lys
 1               5

<210> SEQ ID NO 5
<211> LENGTH: 4
<212> TYPE: PRT
<213> ORGANISM: bovine

<400> SEQUENCE: 5

Ala Leu Pro Met
 1

<210> SEQ ID NO 6
<211> LENGTH: 7
<212> TYPE: PRT
<213> ORGANISM: bovine

<400> SEQUENCE: 6

Trp Glu Asn Gly Glu Cys Ala
 1               5

<210> SEQ ID NO 7
<211> LENGTH: 8
<212> TYPE: PRT
<213> ORGANISM: bovine

<400> SEQUENCE: 7

Trp Glu Asn Gly Glu Cys Ala Gln

```
                1               5

<210> SEQ ID NO 8
<211> LENGTH: 9
<212> TYPE: PRT
<213> ORGANISM: bovine

<400> SEQUENCE: 8

Trp Glu Asn Gly Glu Cys Ala Gln Lys
 1               5

<210> SEQ ID NO 9
<211> LENGTH: 11
<212> TYPE: PRT
<213> ORGANISM: bovine

<400> SEQUENCE: 9

Thr Pro Glu Val Asp Asp Glu Ala Leu Glu Lys
 1               5                  10

<210> SEQ ID NO 10
<211> LENGTH: 8
<212> TYPE: PRT
<213> ORGANISM: bovine

<400> SEQUENCE: 10

Leu Ile Val Thr Gln Thr Met Lys
 1               5

<210> SEQ ID NO 11
<211> LENGTH: 7
<212> TYPE: PRT
<213> ORGANISM: bovine

<400> SEQUENCE: 11

Ala Leu Pro Met His Ile Arg
 1               5

<210> SEQ ID NO 12
<211> LENGTH: 6
<212> TYPE: PRT
<213> ORGANISM: bovine

<400> SEQUENCE: 12

Ile Pro Ala Val Phe Lys
 1               5

<210> SEQ ID NO 13
<211> LENGTH: 6
<212> TYPE: PRT
<213> ORGANISM: bovine

<400> SEQUENCE: 13

Val Ala Gly Thr Trp Tyr
 1               5

<210> SEQ ID NO 14
<211> LENGTH: 10
<212> TYPE: PRT
<213> ORGANISM: bovine

<400> SEQUENCE: 14

Val Leu Val Leu Asp Thr Asp Tyr Lys Lys
 1               5                  10
```

```
<210> SEQ ID NO 15
<211> LENGTH: 9
<212> TYPE: PRT
<213> ORGANISM: bovine

<400> SEQUENCE: 15

Val Leu Val Leu Asp Thr Asp Tyr Lys
 1               5

<210> SEQ ID NO 16
<211> LENGTH: 14
<212> TYPE: PRT
<213> ORGANISM: bovine

<400> SEQUENCE: 16

Thr Pro Glu Val Asp Asp Glu Ala Leu Glu Lys Phe Asp Lys
 1               5                  10

<210> SEQ ID NO 17
<211> LENGTH: 16
<212> TYPE: PRT
<213> ORGANISM: bovine

<400> SEQUENCE: 17

Ala Ala Ser Asp Ile Ser Leu Leu Asp Ala Gln Ser Ala Pro Leu Arg
 1               5                  10                  15

<210> SEQ ID NO 18
<211> LENGTH: 14
<212> TYPE: PRT
<213> ORGANISM: bovine

<400> SEQUENCE: 18

Leu Ser Phe Asn Pro Thr Gln Leu Glu Glu Gln Cys His Ile
 1               5                  10

<210> SEQ ID NO 19
<211> LENGTH: 20
<212> TYPE: PRT
<213> ORGANISM: bovine

<400> SEQUENCE: 19

Ser Leu Ala Met Ala Ala Ser Asp Ile Ser Leu Leu Asp Ala Gln Ser
 1               5                  10                  15

Ala Pro Leu Arg
             20

<210> SEQ ID NO 20
<211> LENGTH: 20
<212> TYPE: PRT
<213> ORGANISM: bovine

<400> SEQUENCE: 20

Val Tyr Val Glu Glu Leu Lys Pro Thr Pro Glu Gly Asp Leu Glu Ile
 1               5                  10                  15

Leu Leu Gln Lys
             20

<210> SEQ ID NO 21
<211> LENGTH: 14
<212> TYPE: PRT
<213> ORGANISM: bovine

<400> SEQUENCE: 21
```

Leu Ser Phe Asn Pro Thr Gln Leu Glu Glu Gln Cys His Ile
 1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Cys Phe Lys Ile Asp Ala Leu Asn Glu Asn Lys Val Ser Arg
 1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Cys Asn Lys Val Leu Val Leu Asp Thr Asp Tyr Lys Lys Tyr Ser
 1               5                   10                  15

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: synthetic
      peptidee

<400> SEQUENCE: 24

Cys Phe Lys Ile Asp Ala Leu Asn Glu Asn Lys Val Leu Val Leu Asp
 1               5                   10                  15

Thr Asp Tyr Lys Lys Tyr Ser
            20

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Leu Ile Val Thr Gln Thr Met Lys Ser Arg Cys
 1               5                   10

<210> SEQ ID NO 26
<211> LENGTH: 28
<212> TYPE: DNA
<213> ORGANISM: Lactobacillus bulgaricus

<400> SEQUENCE: 26
ttttgtggat ccttaacttc atagcacg                                          28

<210> SEQ ID NO 27
<211> LENGTH: 27
<212> TYPE: DNA
<213> ORGANISM: Lactobacillus bulgaricus -continued

```
<400> SEQUENCE: 27
atattatcta gaattgaata gattgcc                                              27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 28
gcggatccgg cttgggcggt gcagatg                                              27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 29
cgcaagcttg tgcgaagtgt tcatggc                                              27
```